United States Patent
Ren et al.

(10) Patent No.: US 12,134,815 B2
(45) Date of Patent: Nov. 5, 2024

(54) IMPLANT-SPECIFIC MEDICAL TITANIUM ALLOY ACHIEVING IMMEDIATE IMPLANT PLACEMENT AND PREPARATION METHOD FOR IMPLANT-SPECIFIC MEDICAL TITANIUM ALLOY

(71) Applicant: INSTITUTE OF METAL RESEARCH, CHINESE ACADEMY OF SCIENCES, Shenyang (CN)

(72) Inventors: Ling Ren, Shenyang (CN); Ke Yang, Shenyang (CN); Shuyuan Zhang, Shenyang (CN); Hai Wang, Shenyang (CN); Sharafadeen Kunle Kolawole, Shenyang (CN); Ziqing Sun, Shenyang (CN)

( * ) Notice: Subject to any disclaimer, the term of this patent is extended or adjusted under 35 U.S.C. 154(b) by 358 days.

(21) Appl. No.: 17/618,356

(22) PCT Filed: Feb. 28, 2020

(86) PCT No.: PCT/CN2020/000038
§ 371 (c)(1),
(2) Date: Dec. 10, 2021

(87) PCT Pub. No.: WO2020/238219
PCT Pub. Date: Dec. 3, 2020

(65) Prior Publication Data
US 2023/0066250 A1    Mar. 2, 2023

(30) Foreign Application Priority Data
May 29, 2019 (CN) .......................... 201910456596.9

(51) Int. Cl.
*C22F 1/18*    (2006.01)
*A61L 27/04*    (2006.01)
*A61L 27/06*    (2006.01)
*C22C 14/00*    (2006.01)

(52) U.S. Cl.
CPC ............ *C22F 1/183* (2013.01); *A61L 27/047* (2013.01); *A61L 27/06* (2013.01); *C22C 14/00* (2013.01); *A61L 2430/12* (2013.01)

(58) Field of Classification Search
CPC ................................. C22C 14/00; C22F 1/183
See application file for complete search history.

(56) References Cited

PUBLICATIONS

English Abstract and English Machine Translation of Feng et al. (CN 101705390 A) (Jun. 12, 2010).*

* cited by examiner

*Primary Examiner* — Jessee R Roe
(74) *Attorney, Agent, or Firm* — Tsz Lung Yeung

(57) ABSTRACT

The present invention relates to the field of medical titanium alloy materials, and in particular, to a narrow-diameter high-strength implant-specific medical titanium alloy achieving immediate implant placement and a preparation method for the implant-specific medical titanium alloy. The medical titanium alloy is prepared from the following chemical components (by weight percentage), 14%-17% of Zr, 3.0%-10% of Cu, and the balance of Ti. The preparation method for the medical titanium alloy comprises: after cogging and forging and before rolling, performing heat preservation for 0.5-6 h at the temperature of 900-1200° C., and water cooling to the room temperature; and rolling at the temperature of 720-850° C., a strain rate being larger than 0.1 s−1, and a barstock obtained after rolling being used for subsequent implant processing. According to the narrow-diameter high-strength implant-specific medical titanium alloy achieving immediate implant placement provided in the present invention, immediate implant placement can be achieved without any surface treatment, and a firm combination of the implant and a bone tissue is achieved. According to the preparation method for the medical titanium alloy provided in the present invention, the implant having a narrow diameter (3.0-3.5 mm) can be prepared and is high in strength, and the purpose of firm implanting on a narrow teethridge missing a tooth is achieved.

5 Claims, 3 Drawing Sheets

IMPLANT-SPECIFIC MEDICAL TITANIUM ALLOY ACHIEVING IMMEDIATE IMPLANT PLACEMENT AND PREPARATION METHOD FOR IMPLANT-SPECIFIC MEDICAL TITANIUM ALLOY

FIELD OF INVENTION

The present invention relates to the field of titanium alloy materials, in particular to an implant-specific medical titanium alloy for immediate implant placement and its preparation method thereof.

DESCRIPTION OF RELATED ARTS

Dental implantation is the greatest research progress in dentistry in the 20th century. It has become the most preferred treatment of dentition defect/loss and has been widely used. Artificial dental implants are considered to be the third set of human teeth. In China, the number of patients with dentition defect accounts for 20-30% of the total number, and the current growth rate of the implant market in China is more than 30%. It is estimated that the dental implants in China will reach 2 to 3 million dental implants per year around 2020. The key to the success of the implant is its firm integration with bone tissue. Professor Branemark, the father of modern dental implants, pioneered the concept of osseointegration, which refers to the firm, long-lasting and direct bond that occurs between the living bone tissue of the human body and the titanium implant. That is to say, there is a direct structural and functional connection between the surface of the force-loaded implant and the viable bone tissue. There is no connective tissue between the implant and the bone tissue, and there is no separation of any tissue. In order to achieve rapid osseointegration, the implant surface treatment technology has been developed from TPS (titanium slurry spraying) in 1974, SLA (Sand Blasting and Acid Etching) in 1994 to the current active hydrophilic SLActive surface, which achieved the goal of immediate implantation and bone healing in 3 weeks. The so-called immediate implant placement (immediate implant placement) refers to the implantation of artificial implants immediately after tooth extraction, without waiting for 4-6 months after wound healing, so the immediate implant placement can shorten the course of treatment and prevent alveolar bone resorption. However, this type of implant is expensive, about 10,000 to 30,000 yuan per implant, which is difficult for ordinary patients to bear. At the same time, the surface treatment process of this immediate implant is complicated and cumbersome, and the cost is high. Therefore, the development of implants that can be implanted immediately without surface treatment can greatly reduce costs, reduce the economic and mental burden of patients, and provide a new direction for the future development of implants.

Due to its good overall performance, especially biocompatibility, the main material of dental implants is commercial pure titanium (CP Ti). However, in some cases the tensile strength of CP Ti cannot meet the requirements. For example, when implanting a tooth on a narrow edentulous gum, a small diameter implant is the first choice. However, reducing the diameter means increasing the risk of breakage. Therefore, it is necessary to develop small-diameter high-strength implants. Although titanium alloys such as Ti-6Al-4V and Ti-6Al-7Nb have higher strength than CP Ti, both of these alloys contain Al element, which will affect the biocompatibility of implants to a certain extent. This in turn affects the ability to implant immediately.

In summary, the present invention will provide a special medical titanium alloy for realizing immediate planting of a narrow-diameter high-strength implant and a preparation method thereof, thus realizing the unification of implant biological function and structural mechanics, improving the function and effectiveness of implants, and providing a new foundation and opportunity for the development of domestic implants.

SUMMARY OF THE PRESENT INVENTION

An object of the present invention is to provide an implant-specific medical titanium alloy for immediate implant placement and its preparation method thereof so that the unification of the biological function and structural mechanics of the implant is realized, and the functionality and effectiveness of the implant is improved.

The technical solution of the present invention is:

A medical titanium alloy, which is narrow-diameter high-strength implant-specific, for realizing immediate implant placement, by weight percentage, a chemical composition of the titanium alloy is: Zr: 14-17; Cu: 3.0-10; the remainder is Ti.

According to a preferred technical solution: the copper content is, by weight percentage, Cu: 6-8.

The present invention also provides a preparation method of the above-mentioned medical titanium alloy. The medical titanium alloy obtained by smelting adopts the following hot working and heat treatment processes:

First Heat Treatment:
  before rolling and after billet forging, insulate at 900-1200° C. environment for 0.5-6 h, and water cool to room temperature.

The Second Hot Working:
  rolling at 720-850° C. environment, a strain rate is greater than 0.1 $s^{-1}$, and the bar obtained after rolling is used for subsequent implant processing.

The titanium alloy manufactured by this method does not require any surface treatment.

The titanium alloy of narrow diameter implant manufactured by this method has a diameter range of 3.0-3.5 mm.

The advantageous effects of the present invention are:

1. According to the narrow-diameter high-strength implant-specific medical titanium alloy for realizing immediate implant placement of the present invention, by adding Cu element, immediate implant placement is realized without any surface treatment, and a firm bonding of the implant and the bone tissue is achieved.

2. According to the preparation method of the narrow-diameter high-strength implant-specific medical titanium alloy for realizing immediate implant placement of the present invention, after billet forging and before rolling, a solution heat treatment is performed, and then hot working is performed. Through this method, the strength of the medical titanium alloy provided by the present invention is improved, and the nano-precipitated phases $Ti_2Cu$ and $Zr_2Cu$ precipitated in the structure play the role of immediate placement.

3. According to the preparation method of the narrow-diameter high-strength implant-specific medical titanium alloy for realizing immediate implant placement of the present invention, narrow diameter (3.0-3.5 mm) implants with high strength can be prepared, thus the objective of firm implantation on narrow edentulous gum can be realized.

DETAILED DESCRIPTION OF THE PREFERRED EMBODIMENT OF THE PRESENT INVENTION

The present invention is further described by means of the following embodiments. These embodiments are merely descriptions of the best embodiments of the present invention, and do not limit the scope of the present invention in any way.

Embodiments: Embodiments 1-6 are medical material titanium alloys containing Cu element, and their chemical compositions are shown in Table 1. The controlled smelting is carried out according to the chemical composition range of the present invention, Also, the heat treatment and thermal processing technology are carried out as follows:

First heat treatment: after billet forging and before rolling into a bar, carryout heat preservation at 900-1200° C. environment for 0.5-6 h, and water cool to room temperature.

The second hot working: rolling at 720-850° C. environment, a strain rate is greater than 0.1 s$^{-1}$, and the bar material obtained after rolling is used for subsequent implant processing.

Comparative Examples

Comparative Examples 1 and 2 are conventional medical titanium alloy TiZr, Comparative Examples 3 and 4 are medical titanium alloys containing a small amount of Cu element, and Comparative Examples 5 and 6 are medical titanium alloys containing a large amount of Cu element. Their chemical compositions are shown in the Table 1. Wherein, Comparative Examples 1, 3, and 5 have undergone the hot working heat treatment process provided by the present invention; Comparative Examples 2, 4, and 6 have undergone conventional hot working heat treatment processes: after billet forging, rolling at 700~850° C. into bar materials.

1. Evaluation of Immediate Implant Placement Ability

Figure 1:
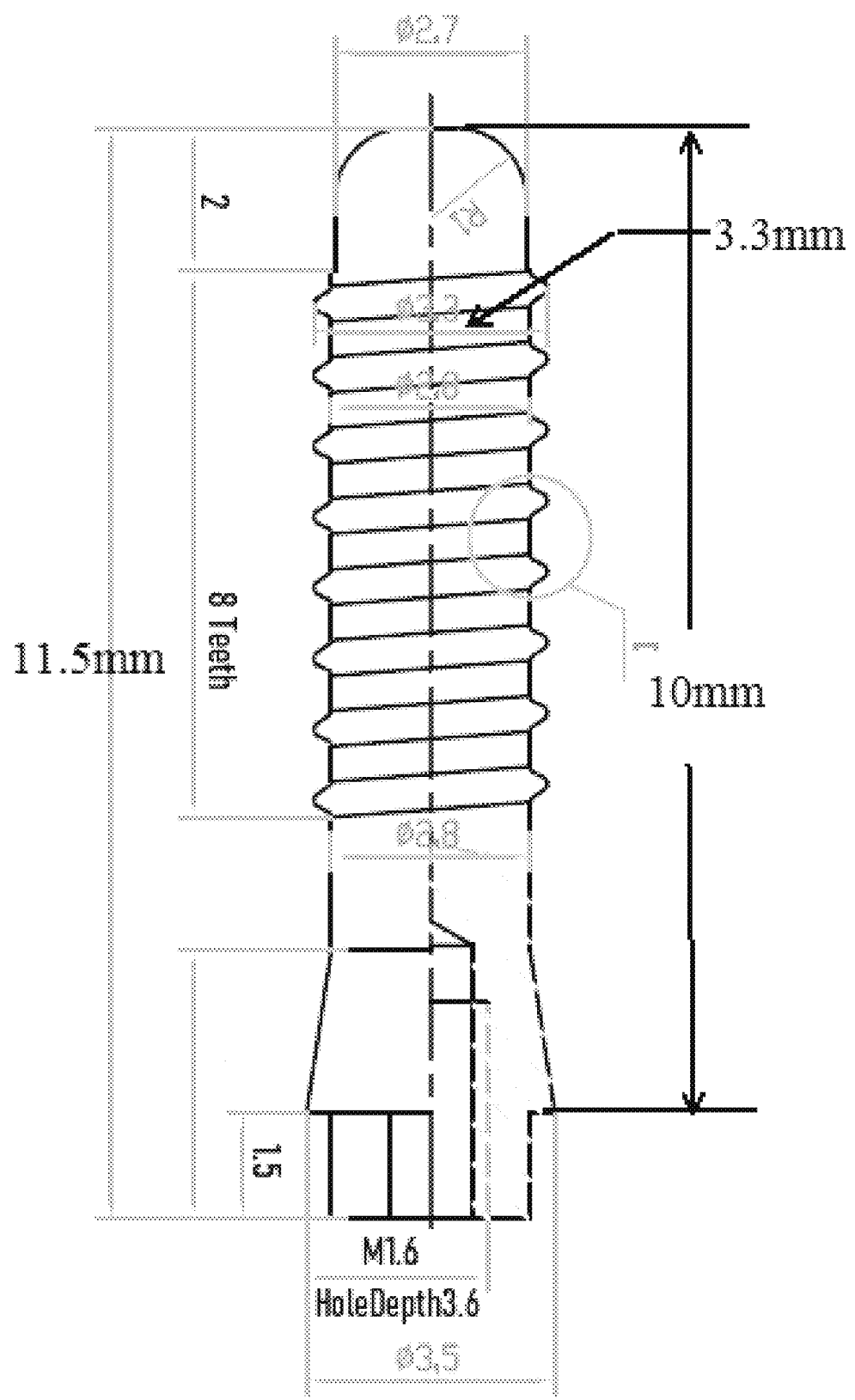
FIG. 1 illustrates a processing design drawing of an implant.
Figure 2:
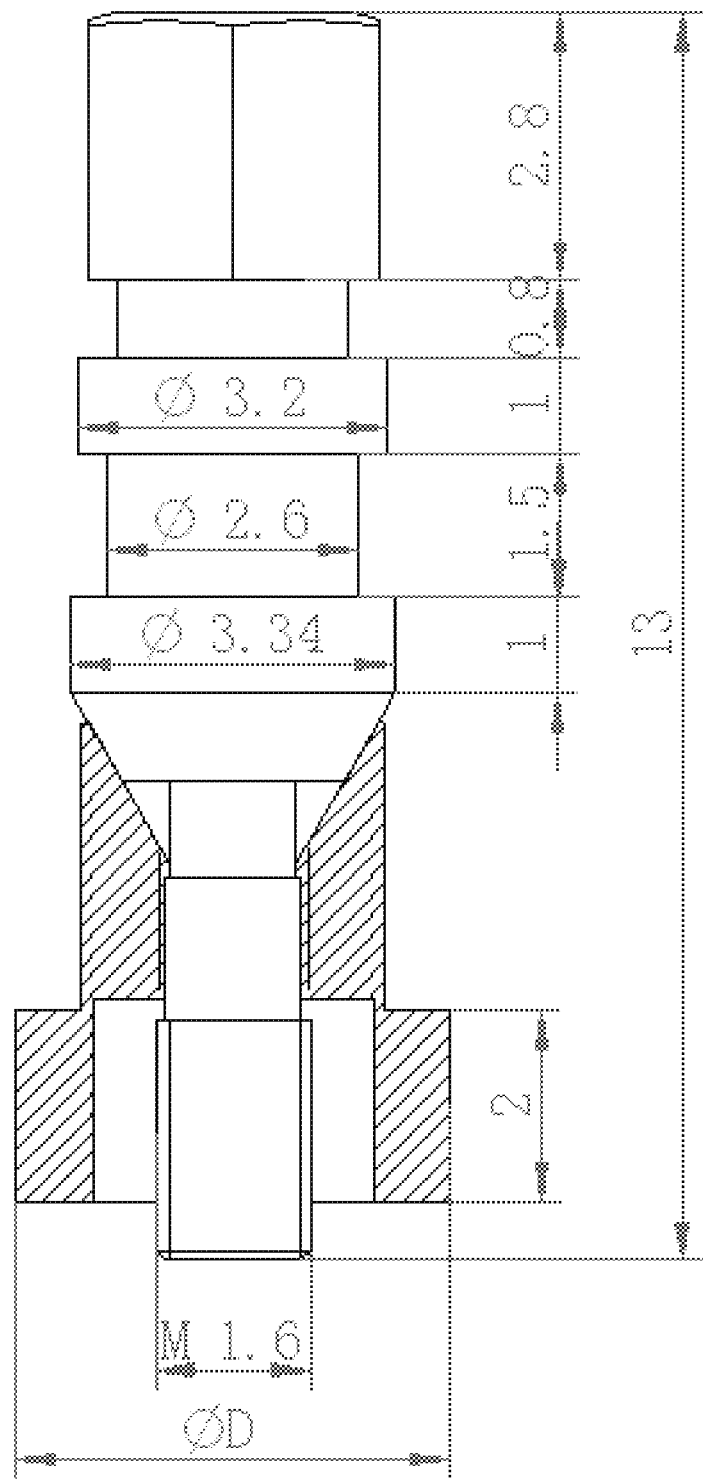
FIG. 2 illustrates a carrier processing design drawing of an implant.

All the bar materials (diameter 4 mm) of the comparative examples and the embodiment of the present invention are processed into threaded implants with reference to the current clinical mainstream Straumann SLA 3.3*10 mm NN SP implant (Straumann company, Switzerland), but no surface treatment is performed. The dimensional design drawings of the implant and the carrier are shown in FIG. 1, and the processed implant, the carrier and the healing abutment are shown in FIG. 2. Then animal experiments are carried out to evaluate the immediate placement ability.

TABLE 1

The chemical composition of the materials of the embodiments and comparative examples (wt. %)

| Materials | Zr | Cu | Ti |
|---|---|---|---|
| Embodiment 1 | 15.7 | 3.9 | Remainder |
| Embodiment 2 | 16.1 | 5.3 | Remainder |
| Embodiment 3 | 15.5 | 6.5 | Remainder |
| Embodiment 4 | 15.8 | 7.3 | Remainder |
| Embodiment 5 | 15.9 | 8.2 | Remainder |
| Embodiment 6 | 15.9 | 9.5 | Remainder |
| Comparative Example 1 | 15.5 | — | Remainder |
| Comparative Example 2 | 16.1 | — | Remainder |
| Comparative Example 3 | 15.7 | 0.6 | Remainder |
| Comparative Example 4 | 15.2 | 1.2 | Remainder |
| Comparative Example 5 | 16.3 | 15.5 | Remainder |
| Comparative Example 6 | 15.9 | 16.1 | Remainder |

Figure 3:
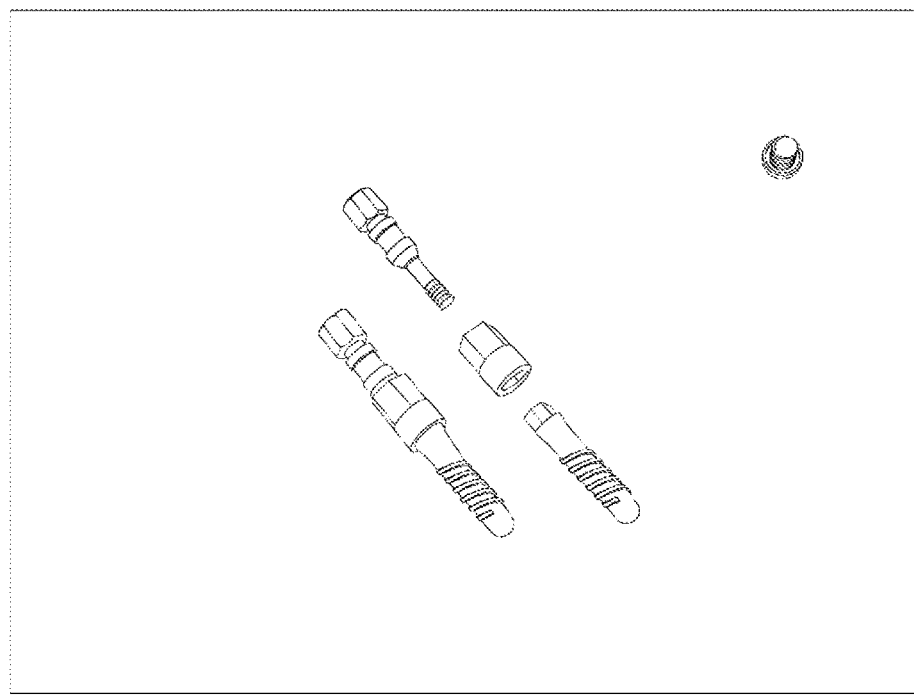
FIG. 3 illustrates an implant, a connector and a healing abutment.
Figure 4:
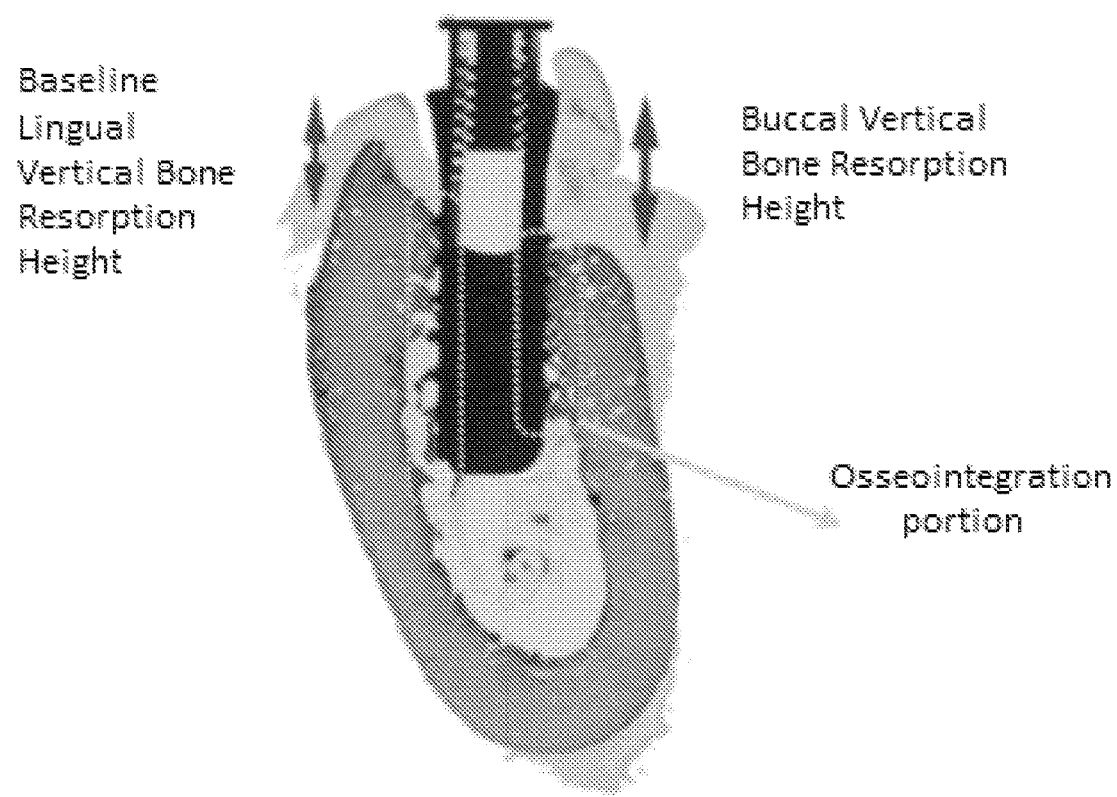
FIG. 4 illustrates a staining observation of hard tissue sections of tissues around an implant.

After extraction of bilateral mandibular premolars, implant surgery is performed after 3 months of natural healing. A standard twist drill was used to prepare a hole at the implant placement site, with a diameter of 3.3 mm and a depth of 10 mm. The above processed implants of the comparative examples and the embodiments are respectively implanted into the edentulous area of the mandible on both sides of the Beagles. The implantation depth is 10 mm, the implant shoulder is flush with the alveolar ridge top bone surface, and then the screw is closed and tightened, the mucosa is pulled up, and the suture is closed tightly. After the operation, start feeding with normal soft food. One week after implantation, the animals are sacrificed for sampling, and hard tissues are sliced and stained with Masson's tricolor staining kit (BASO, Zhuhai, China). Stain the slices with Weigert iron hematoxylin (Weigert iron hematoxylin A, B solution in equal proportions) for 5-10 minutes, and then rinse slightly with running water; differentiate with 1% hydrochloric acid alcohol, and rinse with running water for several minutes. Dye with Ponceau S acid red solution for 5-10 minutes, wash with running water; treat with phosphomolybdic acid solution for 5 minutes, directly use aniline blue dye solution without washing for 5 minutes; treat with 1% glacial acetic acid for 1 minute, dehydrate with 95% alcohol for multiple times; dehydrate with anhydrous alcohol, and mount with neutral gum. The stained sections are observed and photographed with a LeicaS (Typ 007) camera (Leica, Wetzlar, Germany) and an inverted fluorescence microscope (Leica, Heidelberg, Germany), which are shown in FIG. 3. The bone-implant contact (bone-implant contact, BIC) of the implants of the comparative examples and the embodiments are calculated to evaluate the immediate implant placement ability. Implant BIC (%) is defined as the bone length in direct contact with the implant surface divided by the total implant length. The results are shown in Table 2.

2. Mechanical Performance Evaluation

The mechanical properties of the bar materials of the embodiments and comparative examples are examined. The HTV-1000 hardness tester is used to measure the Vickers hardness of the annealed sample. The sample surface is polished before the experiment. The sample size is a sheet with a diameter of 10 mm and a thickness of 2 mm. The test load force is 9.8 N and the pressure duration is 15 s. By measuring the diagonal length of the indentation, the hardness value is automatically calculated by the computer hardness analysis software. The final hardness value is taken as the average value of fifteen points, and three parallel samples are selected for each group of samples. The Instron 8872 tensile testing machine is used to test the room temperature tensile mechanical properties of the samples after heat treatment, and the tensile rate is 0.5 mm/min. Before the experiment, a lathe is used to process the sample into a standard tensile specimen with a thread diameter of 10 mm, a gauge length of 5 mm, and a gauge length of 30 mm. Three parallel samples are taken from each group of the samples after heat treatment, and the mechanical properties indicators obtained in the experiment are tensile strength, yield strength and elongation. The results are shown in Table 2.

3. Cytotoxicity Assessment

The biosafety performance test is carried out on the materials of the embodiments and comparative examples. MTS reagent is used for cytotoxicity experiment. This reagent can be converted into water-soluble formazan compounds by dehydrogenases in living cells, but dead cells have no such function. The cells in the culture flask are digested with trypsin to prepare a cell suspension with a concentration of $5\times10^4$/ml, which is added to a 96-well plate, and 100 μl is added to each well. After culturing for 8 hours in a 5% $CO_2$ incubator, aspirate the original medium, wash gently with PBS twice, add 100 μl of material extract, and set a negative control group (add complete medium) and a positive control group (complete medium containing 10% DMSO). Put the 96-well plate back into the $CO_2$ incubator and continue culturing for 24 h, 48 h and 72 h. At the preset time point, take out the 96-well plate, add 10 μl MTS (Signalway Antibody, USA), incubate for 4 h in the incubator, measure the absorbance value at the 490 nm wavelength of the microplate reader, and calculate the relative growth rate (Relative growth rate, RGR), RGR=(experimental group OD value/culture medium OD value)×100%, and then classify according to the 5-level toxicity evaluation standard (0.1 level meets the requirements of biomedical materials). The results are shown in Table 2.

It can be seen from the results in Table 2 that when the content of Cu element in the medical titanium alloy is low (Comparative Examples 1-4), the BIC value is low, all lower than 40%. According to literature and clinical reports, only when the BIC is greater than 45%, the implant is considered to be well integrated and the implantation is successful. Although the Cu content in Comparative Examples 5 and 6 is relatively high, too much Cu will affect the biocompatibility of the material, that is, the cytotoxicity rating is only Grade 3, which leads to a decrease in the osseointegration rate, both of which are lower than 30%. Only when the weight percentage of Cu element is between 3-10, the BIC exceeds 45%, and it has the highest BIC in the preferred range of Cu element, which proves that it has excellent osseointegration ability and realizes immediate implant placement.

TABLE 5

Related Performance Test Results of Materials of Embodiments and Comparative Examples

| Materials | bone-implant contact (BIC) % | Mechanical Performance | | | | | Cytotoxicity Grading (≤ grade 2 is pass) |
| --- | --- | --- | --- | --- | --- | --- | --- |
| | | $\sigma_b$ MPa | $\sigma_{0.2}$ MPa | δ % | Ψ % | HV 0.5 | |
| Embodiment 1 | 53 | 735 | 643 | 35 | 40 | 330 | 1 |
| Embodiment 2 | 60 | 865 | 755 | 30 | 35 | 345 | 1 |
| Embodiment 3 | 80 | 956 | 853 | 25 | 30 | 360 | 0 |
| Embodiment 4 | 82 | 1012 | 910 | 25 | 30 | 365 | 0 |
| Embodiment 5 | 62 | 1105 | 980 | 15 | 20 | 370 | 1 |
| Embodiment 6 | 59 | 1125 | 1005 | 10 | 12 | 375 | 1 |
| Comparative Example 1 | 32 | 510 | 420 | 35 | 42 | 280 | 0 |
| Comparative Example 2 | 29 | 450 | 345 | 30 | 38 | 290 | 0 |
| Comparative Example 3 | 40 | 720 | 658 | 30 | 35 | 315 | 1 |
| Comparative Example 4 | 39 | 530 | 475 | 28 | 25 | 300 | 1 |
| Comparative Example 5 | 30 | 985 | 858 | 10 | 15 | 355 | 3 |
| Comparative Example 6 | 28 | 855 | 750 | 8 | 10 | 345 | 3 |

It can be seen from the results in Table 2 that when Comparative Examples 1 and 2 are respectively subjected to the hot working and heat treatment process provided by the present invention and conventional method, the mechanical properties of Comparative Example 1 are better than those of Comparative Example 2. At the same time, for Comparative Examples 3 and 4, which are also low-content Cu elements, and Comparative Examples 5 and 6, which are also high-content Cu elements, after respectively undergoing the hot working and heat treatment process provided by the present invention and conventional method, the mechanical properties of Comparative Examples 3 and 5 are better than those of Comparative Examples 4 and 6. Finally, all the embodiments have better mechanical properties after undergoing the hot working and heat treatment process provided by the present invention, and the strength is improved on the basis of maintaining excellent plasticity, which is significantly higher than the comparative examples.

It can be seen from the above analysis that when the content of Cu element is in the preferred range, after the hot working and heat treatment process provided by the present invention, the implant-specific medical titanium alloy provided by the present invention not only achieves the purpose of immediate implant placement, but also has a higher strength and a better biocompatibility.

Details not provided by the present invention is known technologies.

The above-mentioned embodiments are only to illustrate the technical concept and characteristics of the present invention, and the purpose is to enable those familiar with the technology to understand the content of the present invention and implement them accordingly, and cannot limit the protection scope of the present invention. All equivalent changes or modifications made according to the spirit of the present invention should be covered within the protection scope of the present invention.

What is claimed is:

1. An implant-specific medical titanium alloy for realizing immediate implant placement, characterized in that: by weight percentage, a chemical composition of the titanium alloy is: Zr: 14-17; Cu: 6-8; the remainder is Ti.

2. A preparation method of the implant-specific medical titanium alloy for realizing immediate implant placement, characterized in that: before rolling and after billet forging, insulating at 900-1200° C. environment for 0.5-6 h, and water cooling to room temperature, wherein, by weight percentage, a chemical composition of the titanium alloy is: Zr: 14-17; Cu: 3.0-10; the remainder is Ti.

3. The preparation method of the implant-specific medical titanium alloy for realizing immediate implant placement according to claim 2, characterized in that: rolling at 720-850° C. environment with a strain rate greater than $0.1 \text{ s}^{-1}$ to obtain a bar materials after rolling for subsequent implant processing.

4. The preparation method of the implant-specific medical titanium alloy for realizing immediate implant placement according to claim 2, characterized in that: no surface treatment of the titanium alloy is required.

5. The preparation method of the implant-specific medical titanium alloy for realizing immediate implant placement according to claim 2, characterized in that: the titanium alloy is a narrow-diameter implant with a diameter range of 3.0-3.5 mm.

* * * * *